(12) United States Patent
Bourdon et al.

(10) Patent No.: US 10,307,362 B2
(45) Date of Patent: Jun. 4, 2019

(54) DERMAL INJECTABLE STERILE COMPOSITION

(71) Applicant: TEOXANE, Geneva (CH)

(72) Inventors: François Bourdon, Gaillard (FR);
Stéphane Meunier, Thoiry (FR)

(73) Assignee: TEOXANE SA, Geneva (CH)

( * ) Notice: Subject to any disclaimer, the term of this patent is extended or adjusted under 35 U.S.C. 154(b) by 0 days.

(21) Appl. No.: 15/874,144

(22) Filed: Jan. 18, 2018

(65) Prior Publication Data

US 2018/0140530 A1    May 24, 2018

Related U.S. Application Data

(62) Division of application No. 14/437,917, filed as application No. PCT/IB2013/059607 on Oct. 24, 2013, now Pat. No. 9,907,739.

(30) Foreign Application Priority Data

Oct. 24, 2012   (FR) ...................... 12 60146

(51) Int. Cl.

| | | |
|---|---|---|
| *A61Q 19/00* | (2006.01) | |
| *A61K 8/73* | (2006.01) | |
| *A61K 31/728* | (2006.01) | |
| *C08B 37/08* | (2006.01) | |
| *C08L 5/08* | (2006.01) | |
| *A61Q 19/08* | (2006.01) | |
| *A61K 8/04* | (2006.01) | |

(52) U.S. Cl.
CPC .............. *A61K 8/735* (2013.01); *A61K 8/042* (2013.01); *A61K 31/728* (2013.01); *A61Q 19/08* (2013.01); *C08B 37/0072* (2013.01); *C08L 5/08* (2013.01); *A61K 2800/91* (2013.01); *A61Q 19/00* (2013.01)

(58) Field of Classification Search
CPC ...... A61K 8/735; A61K 31/728; A61K 8/042; A61K 2800/91; C08B 37/0072; C08L 5/08; A61Q 19/08; A61Q 19/00
USPC ........................................................ 514/54
See application file for complete search history.

(56) References Cited

U.S. PATENT DOCUMENTS

| | | | | |
|---|---|---|---|---|
| 2004/0162235 A1* | 8/2004 | Trubetskoy | .......... | A61K 31/713 514/44 R |
| 2006/0105022 A1 | 5/2006 | Yokokawa et al. | | |
| 2007/0036745 A1 | 2/2007 | Leshchiner et al. | | |
| 2011/0256059 A1 | 10/2011 | Sanchez Barreiro et al. | | |
| 2013/0203856 A1 | 8/2013 | Cho et al. | | |

FOREIGN PATENT DOCUMENTS

| | | |
|---|---|---|
| CA | 2805008 A1 | 1/2012 |
| FR | 2752843 A1 | 3/1998 |
| RU | 2230752 C2 | 6/2004 |
| WO | WO-00/27887 A2 | 5/2000 |
| WO | WO-2006/048671 A1 | 5/2006 |
| WO | WO-2006/056204 A1 | 6/2006 |
| WO | WO-2008/015249 A2 | 2/2008 |
| WO | WO-2010/049562 A1 | 5/2010 |
| WO | WO-2011/135150 A1 | 11/2011 |
| WO | WO-2012/008722 A2 | 1/2012 |

OTHER PUBLICATIONS

Yan et al., "Improved synthesis of hyaluronic acid hydrogel and its effect on tissue augmentation". Journal of Biomaterials Applications, 0(0) 1-9, 2011.
Kuo et al., "Chemical Modification of Hyaluronic Acid by Carbodiimides", Bioconjugate Chem., 1991, 2, 232-241.
Di Meo et al., "Synthesis and NMR Characterization of New Hyaluronan-Based NO Donors", Biomacromolecules, 2006, 7, 1253-1260.
Magnani et al., "Novel Polysaccharide Hydrogels: Characterization and Properties", Polymers for Advanced Technologies, 11, 488-495 (2000).
Bulpitt et al., "New strategy for chemical modification of hyaluronic acid: Preparaton of functionalized derivatives and their use in the formation of novel biocompatible hydrogels", Journal of Biomedical Materials Research, vol. 47, No. 2, Jan. 1, 1999, pp. 153-169.
Bergman et al., "Hyaluronic Acid Derivatives Prepared in Aqueous Media by Triazine-Activated Amidation", Biomacromolecules, 2007, 8, 2190-2195.
Office Action dated Sep. 21, 2017 in counterpart Russian application 2015118969/13(029436) and its English translation.

* cited by examiner

*Primary Examiner* — Yih-Horng Shiao
(74) *Attorney, Agent, or Firm* — Polsinelli PC

(57) ABSTRACT

The present invention relates to a crosslinked hyaluronic acid gel which derives from the crosslinking of hyaluronic acid or of a salt thereof in the presence of at least an effective amount of at least one endogenous polyamine as a crosslinking agent, said crosslinking being carried out under conditions favorable to the coupling of said hyaluronic acid and of said endogenous polyamine(s).

7 Claims, No Drawings

DERMAL INJECTABLE STERILE COMPOSITION

CROSS REFERENCE TO RELATED APPLICATIONS

This application is a Divisional of U.S. application Ser. No. 14/437,917 filed on Oct. 24, 2013, which is the National Phase filing under 35 U.S.C. § 371 of PCT/IB2013/059607 filed on Oct. 24, 2013; and this application claims priority to Application No. 1260146 filed in France on Oct. 24, 2012. The entire contents of each application are hereby incorporated by reference.

The present invention relates to the field of sterile injectable compositions based on hyaluronic acid or on a salt thereof and intended for the treatment of skin defects and imperfections.

Hyaluronic acid, which is naturally present in the skin, is known for its viscoelastic properties and also its very high propensity to absorb water. Its properties contribute to a large extent to the elasticity of the skin.

Given its properties and its qualities of biocompatibility, tolerance and lack of toxicity, advantage has thus been taken of this compound for more than 10 years now in many applications in the medical and cosmetics fields, and in particular aesthetic procedures.

Thus, hyaluronic acid is used for filling wrinkles and for reducing, or even eliminating, local weakening of the structure of the dermis represented by a wrinkle or skin depression, generally via a direct injection into the dermis, in the area under consideration.

Unmodified hyaluronic acid is perfectly biocompatible and identical to endogenous hyaluronic acid.

However, hyaluronic acid is used essentially in the form of a gel based on crosslinked hyaluronic acid, and therefore in a modified form given the increased resistance of this particular form to degradation, to heat and therefore to sterilization.

These crosslinked hyaluronic acid gels can be obtained by various preparation processes. Generally, these processes require two main steps, the first consisting in hydrating the hyaluronic acid in order to convert it into an aqueous gel and the second aimed at crosslinking said aqueous gel in the presence of an agent capable of inducing the crosslinking thereof (also referred to as "crosslinking agent"). This agent is usually chosen from epoxide, aldehyde, polyaziridyl or divinylsulphone (DVS), or butanediol diglycidyl ether (BDDE), and is therefore synthetic in nature.

By way of illustration of these processes, mention may in particular be made of those described in documents US 2006/0105022, WO 2006/056204 and US 2007/0036745.

The crosslinked gels currently on the market and obtained with conventional crosslinking agents generally have degrees of modification of greater than 4%, or even degrees of modification up to 10%.

For the purposes of the present invention, the term "degree of modification" is intended to denote the ratio between the number of moles of crosslinking agent attached to the hyaluronic acid and the number of moles of hyaluronic acid forming said crosslinked gel. This quantity can in particular be measured by 1D $^1$H NMR analysis of the crosslinked gel.

The expression "number of moles of hyaluronic acid" is intended to mean the number of moles of repeating disaccharide units of the hyaluronic acid, the disaccharide unit being composed of D-glucuronic acid and D-N-acetylglucosamine linked to one another via alternating beta-1,4 and beta-1,3 glycosidic bonds.

However, with a view to getting as close as possible to endogenous hyaluronic acid, it would be desirable to have crosslinked hyaluronic acid gels with a lower degree of modification.

Admittedly, crosslinked gels with lower degrees of modification (i.e. between 1% and 2%) have already been proposed. Unfortunately, they prove to be poorly cohesive and have a low resistance to crushing. These deficiencies manifest themselves in particular in oscillatory rheology through a restricted viscoelasticity range (the viscoelasticity range is represented by the stress range in which G' remains constant, during a measurement with stress sweep. The extent of this viscoelasticity range can in particular be assessed by measuring the cross-over stress, i.e. the stress at which the value of G' decreases and equals the value of G").

This behaviour is therefore to be improved for applications in filling wrinkles.

More specifically, there remains a need for gels of crosslinked hyaluronic acid with the lowest possible degrees of modification, which at the same time remain satisfactory in terms of the mechanical properties exhibited.

Against all expectations, the inventors have noted that such a gel can be obtained when the crosslinking step is carried out in the presence of a specific type of compound.

Thus, according to a first aspect of the invention, the subject thereof is a crosslinked hyaluronic acid gel which derives from the crosslinking of hyaluronic acid or of a salt thereof in the presence of at least an effective amount of at least one endogenous polyamine as crosslinking agent, said crosslinking being carried out under conditions favourable to the covalent coupling of said hyaluronic acid and of said endogenous polyamine(s).

Admittedly, polyamines, which are nevertheless distinct from those considered according to the invention, have already been proposed for the formation of crosslinked hyaluronic acid hydrogels.

Thus, the publications by Xiang Mei Yuan et al. (Journal of biomaterials Applications 0(0) 1-9; 27 Feb. 2012) and by Junseok Yeom et al. (Bioconjugate Chem., 1991 (2) 232-241), and also application WO 2012/008722, provide hyaluronic acid (HA) hydrogels crosslinked in the presence of hexamethylenediamine (HMDA). However, the polyamine considered, namely hexamethylenediamine (HMDA), is a synthetic diamine and therefore not an endogenous diamine what is more, the amounts of crosslinking agent (HMDA) used in this prior art range between 25% and 72% and result in very high degrees of modification of between 5% and 35%.

The term "amount of crosslinking agent" is intended to denote the ratio between the number of moles of polyamine(s) and the number of moles of hyaluronic acid, used to synthesize the gel.

Finally, as emerges from the examples hereinafter, the HA-HMDA gels prove to be significantly less effective in terms of mechanical properties than those obtained according to the invention.

As regards the endogenous polyamines considered according to the invention, application WO 2008/015249 proposes, for its part, to use them together with hyaluronic acid particles for topical use as an anti-ageing active agent and as an antioxidant. For obvious reasons, such a mixture is very different from the gels considered according to the invention.

The publication by Di Meo et al. (Biomacromolecules, 2006, 7:1253-60) describes the formation of hydrogels via the Ugi reaction or else condensation of hyaluronic acid and spermidine. This therefore involves a mechanism which is different from that considered in the present invention. What is more, the hydrogels thus obtained and not dedicated to a use in accordance with the invention result from a process using high amounts of crosslinking agent (between 5% and 25%).

The inventors have therefore noted that an endogenous polyamine constitutes a crosslinking agent of choice for obtaining a crosslinked hyaluronic acid gel in accordance with the abovementioned expectations, namely which has a reduced degree of modification compared with those observed with crosslinking agents usually considered, and mechanical properties and a resistance to sterilization that are particularly satisfactory.

Indeed, the crosslinked gels according to the invention have a significantly reduced degree of modification, namely less than or equal to 1%, while at the same time remaining satisfactory in terms of mechanical properties.

A crosslinked gel according to the invention also proves to be advantageous in that it consists of compounds that are naturally present in most living organisms and human beings in particular.

From the viewpoint of this pseudonatural nature, it meets an increasing demand by consumers in this respect.

Finally, it is likely that the properties intrinsic to the endogenous polyamines considered according to the invention are preserved within the crosslinked hyaluronic acid gel obtained according to the invention. As it happens, insofar as these properties have an antioxidant effect, or even anti-ageing effect, they are particularly pleasant in the context of the present invention.

According to another aspect of the present invention, the subject thereof is a sterile injectable dermatological composition comprising, in a physiologically acceptable medium, at least one crosslinked hyaluronic acid gel according to the invention.

For the purposes of the present invention, the term "skin" encompasses the skin of the face, of the neck, of the neckline, of the hands, of the scalp, of the abdomen and/or of the legs, but also the lips.

The term "sterile" is intended to qualify an environment capable of guaranteeing the compounds considered in the composition according to the invention, and/or said composition which contains them, the innocuity required for administration in or through the skin, in particular intraepidermal and/or intradermal and/or subcutaneous administration. In particular, it is essential for the composition containing said compounds and which has to be administered according to an injection technique, for example according to the mesotherapy technique, to be devoid of any contaminating body capable of initiating an adverse side reaction in the host organism.

For the purposes of the present invention, the term "injectable" is intended to denote a composition of which the mechanical properties are appropriate for the use considered, namely its administration in or through the skin for, in particular, filling wrinkles.

Thus, a composition according to the invention is injectable via a fine hypodermic needle (in particular with a diameter of less than 18 G, or even less than 27 G), and advantageously has an elastic modulus (G') of between 20 and 1000 Pa, preferably between 40 Pa and 400 Pa, with a phase angle ($\delta$) of less than 45°.

This elastic modulus (G') and the phase angle ($\delta$) are measured via the protocol defined hereinafter.

According to yet another aspect of the present invention, the subject thereof is a dermatological or cosmetic composition comprising at least one crosslinked hyaluronic acid gel according to the invention.

This embodiment, which is not limited in terms of route of administration, consequently permits the administration of said composition topically.

According to another aspect of the present invention, the subject thereof is a kit comprising:
- a packaging containing at least one dose of a crosslinked hyaluronic acid gel according to the invention or of a composition according to the invention; and
- a device for injecting in or through the skin or a device for microperforation of the skin, dedicated to the administration of said dose.

According to yet another aspect of the invention, the subject thereof is the use of a crosslinked gel or of a composition according to the invention, for filling skin volume defects and in particular filling wrinkles.

According to yet another aspect of the invention, the subject thereof is the use of a crosslinked gel or of a composition according to the invention for preventing and/or treating the cutaneous signs of chronological ageing and/or the cutaneous signs which are induced by external factors such as stress, atmospheric pollution, tobacco or prolonged exposure to ultraviolet (UV) radiation.

According to yet another aspect of the invention, the subject thereof is the use of a crosslinked gel or of a composition according to the invention for preventing and/or treating a modification of the surface appearance of the skin.

According to yet another aspect of the invention, the subject thereof is the use of a crosslinked gel or of a composition according to the invention for preventing and/or treating a modification of the viscoelastic or biomechanical properties of the skin.

For the purpose of the present invention, the term "prevention" is intended to mean reducing the risk of occurrence of a phenomenon.

According to another aspect of the invention, the subject thereof is a cosmetic skin treatment process, comprising at least one step of administering, in or through the skin, a crosslinked gel or a composition according to the invention.

According to yet another aspect of the present invention, the latter relates to a process for preparing a crosslinked gel of hyaluronic acid or a salt thereof, comprising at least the steps consisting in:

a) providing an aqueous gel of hyaluronic acid or of a salt thereof, in the noncrosslinked state, b) bringing the gel obtained in step a) into contact with an effective amount of at least one endogenous polyamine, c) crosslinking said mixture formed in step b), said crosslinking being carried out under conditions favourable to the covalent coupling of said hyaluronic acid and of said endogenous polyamine(s), and d) recovering said crosslinked hydrogel.

According to one particular embodiment, the process also comprises a step e) of stopping the crosslinking, consisting in exposing the crosslinked gel to conditions favourable to stopping the crosslinking thereof, it being possible for this step to be carried out before, jointly with or after the recovering step d).

Crosslinked Hyaluronic Acid Gel

As previously indicated, a crosslinked hyaluronic acid gel according to the invention derives from the crosslinking of at least hyaluronic acid or a salt thereof with, as crosslinking agent, at least one endogenous polyamine, said crosslinking being carried out under conditions favourable to the coupling of said hyaluronic acid and of said endogenous polyamine(s).

Hyaluronic acids are linear polysaccharides with alternating D-glucuronic acid and N-acetyl-D-glucosamine units.

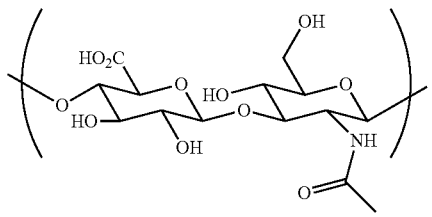

The are naturally present in several tissues and are degraded by hyaluronidases, which are present throughout the body, or via oxidation mechanisms.

For the purpose of the present invention, the term "endogenous polyamine" is intended to denote a polyamine that is naturally present in living organisms and more particularly the human body.

A polyamine according to the invention consequently differs from hexamethylenediamine (HMDA) which is a polyamine of synthetic origin.

By way of representation of endogenous polyamines, mention may quite particularly be made, in animal eukaryotes, of putrescine (or 1,4-diaminobutane), spermidine (or 1,8-diamino-5-azaoctane) and spermine (1,12-diamino-5,9-diazadodecane).

Spermine is a tetraamine and is synthesized from spermidine.

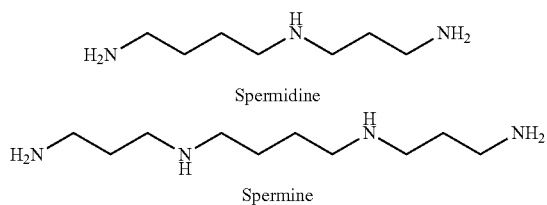

Advantageously, the endogenous polyamine used for obtaining a crosslinked gel according to the invention can be chosen from spermidine, spermine, and a mixture thereof, and better still spermine.

This selection is all the more advantageous since spermine and spermidine are involved in numerous fundamental cell mechanisms, such as DNA synthesis and gene expression. Used topically, their beneficial effects on improving the condition of the skin and reducing the signs of ageing have already been described (see in particular application WO 2006/048671). These compounds are also considered to be antioxidants and anti-ageing active agents of choice.

The coupling reaction considered in the present invention to achieve crosslinking reaction between the hyaluronic acid and the endogenous polyamine(s) is carried out by reaction between an amine function and carboxylic acid, thus giving rise to the formation of an amide function.

In other words, the crosslinking reaction considered in the present invention leads to the formation of molecules of crosslinked hyaluronic acid covalently coupled with the endogenous polyamine(s). There is no electrostatic interactions.

Against all expectations, the resulting crosslinked gels, in the light of the degrees of modification considered very reduced, show mechanical properties which are very satisfactory, or even unattainable by means of the conventional processes as mentioned previously.

Thus, according to one particular embodiment, a crosslinked gel according to the invention advantageously has a degree of modification of less than or equal to 1%, preferably between 0.1% and 1%, and better still between 0.4% and 0.8%.

As previously indicated, the "degree of modification" corresponds to the ratio between the number of moles of endogenous polyamine attached to the hyaluronic acid and the number of moles of hyaluronic acid forming said crosslinked gel. This quantity can in particular be measured by 1D $^1$H NMR analysis of the crosslinked gel.

It is recalled that the expression "number of moles of hyaluronic acid" is intended to mean the number of moles of repeating disaccharide units of the hyaluronic acid, the disaccharide unit being composed of D-glucuronic acid and D-N-acetylglucosamine linked to one another via alternating beta-1,4 and beta-1,3 glycosidic bonds.

According to one particular embodiment, a crosslinked gel according to the invention is such that it can comprise from 0.5% to 40% by weight of hyaluronic acid not subjected to the crosslinking reaction, relative to the total amount of hyaluronic acid.

According to another particular embodiment, a crosslinked gel according to the invention can have a hyaluronic acid concentration of between 5 and 30 mg/g.

According to yet another particular embodiment, a crosslinked gel according to the invention can have an elastic modulus (G') of between 20 and 1000 Pa, preferably between 40 Pa and 400 Pa.

According to one particular embodiment, a crosslinked gel according to the invention can be in the form of a predominantly elastic, viscoelastic hydrogel with a phase angle (δ) of less than 45°.

According to one preferred embodiment, a crosslinked gel according to the invention can have an elastic modulus (G') of between 20 and 1000 Pa, preferably between 40 Pa and 400 Pa, combined with a phase angle (δ) of less than 45°.

In particular, a crosslinked hyaluronic acid gel in accordance with the invention can be injectable via a hypodermic needle with a diameter between 34 G and 18 G.

According to yet another particular embodiment, a crosslinked gel according to the invention is highly cohesive. This characteristic manifests itself in particular through a high stress-sweep cross-over stress, of greater than 100 Pa.

The elastic modulus (G', in Pa) and the phase angle (δ, in °) can be measured according to the following protocol:

The measurements are carried out at 25° C. at a frequency of 1 Hz, with a stress sweep using a Thermo Haake RS3000 rheometer with a cone-plate geometry of 1°/35 mm diameter. G' and δ are recorded at an applied deformation stress of 5 Pa, i.e. in the viscoelasticity range where G' and δ remain stable. The value of the cross-over stress (when G' decreases to equal the viscous modulus G") is then also recorded.

For a cohesive gel according to the invention, this cross-over stress is therefore greater than 100 Pa.

Finally, according to one particular embodiment, a crosslinked gel according to the invention can have a high resistance to sterilization (the loss of G' caused by the sterilization is less than 50%).

The sterilization can be carried out in an autoclave (wet heat) at T°≥121° C., so as to obtain an F0>15 (sterilizing value).

As previously indicated, the crosslinking reaction for obtaining a crosslinked gel according to the invention is carried out under conditions favourable to the covalent coupling of said hyaluronic acid and of said endogenous polyamine(s).

For the purpose of the present invention, the term "favourable conditions" is intended to mean an element which initiates said coupling.

The choice of this initiating element is clearly among the skills of those skilled in the art.

Generally, this coupling is carried out via at least one "activator" compound, where appropriate combined with at least one "auxiliary coupling agent".

For example, such an activator can have the function of making the carbon of the carboxyl group of the hyaluronic acid more electrophilic and therefore of thus stimulating its reactivity with regard to one of the amine groups of the endogenous polyamine.

The activator can advantageously be a condensation agent, for example a pyridinium salt, for instance 2-chloro-1-methylpyridinium as described in the document Magnani, A. et al. (Polymers for Advanced Technologies 1 1, 488-495 (2000)), a carbodiimide as described in the document Bulpitt, P. & Aeschlimann (J. of Biomed. Materials Res. 47, 152-169 (1999)), or a triazine derivative as described in the document Bergman et al. (Biomacromolecules 8, 2190-2195 (2007)).

Preferably, such an activator can be chosen from water-soluble carbodiimides, such as 1-ethyl-3-(3-dimethylaminopropyl)carbodiimide (EDC), 1-ethyl-3-(3-trimethylaminopropyl)carbodiimide (ETC), 1-cyclohexyl-3-(2-morpholinoethyl)carbodiimide (CMC), and also salts thereof, and mixtures thereof, and is preferably represented by EDC.

Preferably, an auxiliary coupling agent, when it is present, can be chosen from N-hydroxysuccinimide (NHS), N-hydroxybenzotriazole (HOBt), 3,4-dihydro-3-hydroxy-4-oxo-1,2,3-benzotriazole (HOOBt), 1-hydroxy-7-azabenzotriazole (HAt) and N-hydroxysulphosuccinimide (sulpho NHS), and mixtures thereof, and is preferably represented by HOBt.

Even more preferably, such an activator can be chosen from EDC, where appropriate in combination with HOBt as auxiliary coupling agent.

The EDC makes it possible to activate the carboxylic acid by forming an intermediate with the carboxylate. The addition of HOBt to the reaction medium makes it possible in particular to avoid any epimerization and to promote the reaction.

Process for Preparing a Crosslinked Gel

As indicated above, the present invention also relates to a process for preparing a crosslinked gel of hyaluronic acid or a salt thereof, comprising at least the steps consisting in:
 a) providing an aqueous gel of hyaluronic acid or of a salt thereof, in the noncrosslinked state,
 b) bringing the gel obtained in step a) into contact with an effective amount of at least one endogenous polyamine,
 c) crosslinking said mixture formed in step b), said crosslinking being carried out under conditions favourable to the covalent coupling of said hyaluronic acid and of said endogenous polyamine(s), and
 d) recovering said crosslinked hydrogel.

According to one particular embodiment, the process also comprises a step e) of stopping the crosslinking, consisting in exposing the crosslinked gel to conditions favourable to stopping the crosslinking thereof, it being possible for this step to be carried out before, jointly with or after the recovering step d).

According to one particular embodiment, the crosslinking step c) can be carried out in the presence of at least one activator, optionally combined with at least one auxiliary coupling agent, i.e. compounds which stimulate the reactivity of at least one of the two compounds to be coupled, preferably chosen from those previously mentioned.

This step of adding the activator, and optionally the auxiliary coupling agent, can therefore advantageously be carried out jointly with the crosslinking step c).

According to one particular embodiment, the hyaluronic acid used for obtaining a gel according to the invention may be in salt form.

Preferably, a hyaluronic acid salt may be chosen from the sodium salt, the potassium salt, the zinc salt, the silver salt, and a mixture thereof, preferably the sodium salt.

Advantageously, the hyaluronic acid used for obtaining a gel according to the invention may have an average molecular weight ranging from 50 000 to 10 000 000 daltons, preferably from 500 000 to 4 000 000 daltons.

The adjustment of the amount of hyaluronic acid for carrying out the crosslinking reaction is clearly among the skills of those skilled in the art.

Advantageously, the hyaluronic acid or a salt thereof can be used in a process for preparing a crosslinked gel according to the invention in a content of between 0.5% and 12% by weight, preferably between 1% and 4% by weight, relative to the total weight of the mixture obtained at the end of step b), i.e. before carrying out the crosslinking step c).

The adjustment of the amount of endogenous polyamine(s) for carrying out the crosslinking reaction is clearly among the skills of those skilled in the art.

The amount of crosslinking agent corresponds to the ratio between the number of moles of polyamine(s) and the number of moles of hyaluronic acid, used for synthesizing the gel.

Advantageously, one or more endogenous polyamine(s) may be used in a process for preparing a crosslinked hyaluronic acid gel according to the invention in a content of between 0.1% and 3%, preferably between 0.5% and 1.5% by number of moles of polyamine(s) relative to the number of moles of hyaluronic acid that are present in the reaction medium, i.e. the mixture of step b).

Advantageously, the activator(s), where appropriate combined with one or more auxiliary coupling agent(s), may be used in a process for preparing a crosslinked hyaluronic acid gel according to the invention in a content such that the number of moles of activator(s) and, where appropriate, of auxiliary coupling agent(s), relative to the number of moles of hyaluronic acid of the reaction medium (n activator/n HA) is between 0.1 and 2, preferably between 0.5 and 1.5.

The crosslinked hyaluronic acid gel is obtained by taking into consideration the presence of at least one endogenous polyamine.

Consequently, the crosslinking can be carried out using only this type of crosslinking agent. However, this crosslinking can also be carried out by taking into consideration the simultaneous presence of at least one supplementary, in particular conventional, crosslinking agent.

Advantageously, this supplementary crosslinking agent can then be taken into consideration in a significantly reduced amount compared with those conventionally retained when it is used as sole crosslinking agent.

This supplementary crosslinking agent can be chosen from epoxide, aldehyde, polyaziridyl, polyamines distinct from the endogenous polyamines, polyphosphates, divinyl-sulphone (DVS), and mixtures thereof, preferably from epoxide crosslinking agents, which are preferably bifunctional or multifunctional.

Preferably, the supplementary crosslinking agent can be chosen from epoxide, more particularly from 1,4-butanediol diglycidyl ether (BDDE), diepoxyoctane or 1,2-bis(2,3-epoxypropyl)-2,3-ethylene, 1,4-bis(2,3-epoxypropoxy)butane, 1,4-bisglycidyloxybutane, 1,2-bis(2,3-epoxypropoxy)ethylene, 1-(2,3-epoxypropyl)-2,3-epoxycyclohexane, and mixtures thereof, and better still 1,4-butanediol diglycidyl ether (BDDE).

Moreover, the presence of an inorganic salt of an alkali metal halide can also be considered during the crosslinking reaction.

Indeed, unexpectedly, the inventors have noted that the presence of an inorganic salt of an alkali halide while carrying out the crosslinking reaction makes it possible to further improve the rheological properties of the crosslinked gel for the same degree of crosslinking.

For the purpose of the present invention, the term "salt of an alkali halide" is intended to denote a compound made up of an alkali cation and of an anion necessarily representing a halogen atom.

Advantageously, the halogen atom can be chosen from fluorine, chlorine, bromine and iodine, and is preferably represented by chlorine.

Preferably, an inorganic salt of an alkali halide according to the invention can be chosen from the sodium salts, potassium salts and caesium salts, and better still is represented by a sodium salt.

Even more preferably, an inorganic salt of an alkali halide according to the invention may be NaCl.

NaCl in fact has the advantage of being physiologically acceptable and it is one of the constituents of one of the raw materials which are part of the composition of the crosslinked hyaluronic acid gels.

Advantageously, the inorganic salt(s) of an alkali halide may be used in a process according to the invention in a content of between 0.5% and 20% by weight, preferably between 1% and 10% by weight, relative to the total weight of the mixture obtained at the end of step b).

In the light of the aforementioned, a process for preparing a crosslinked hyaluronic acid gel according to the invention requires, firstly, providing an aqueous gel comprising at least hyaluronic acid in a noncrosslinked form, combined with at least one endogenous polyamine, as a crosslinking agent.

For the purpose of the present invention, the term "non-crosslinked" is intended to denote an aqueous gel of hyaluronic acid which is not crosslinked or not transformed, i.e. a solution of hyaluronic acid of which the chains of the polymer are not connected to one another by strong or covalent bonds.

More specifically, the aqueous gel considered in step a) can be obtained beforehand by bringing together, in an appropriate receptacle:
(i) an aqueous medium;
(ii) at least hyaluronic acid, or a salt thereof, in a non-crosslinked form; and
(iii) where appropriate, at least one endogenous polyamine; and homogenizing the resulting mixture, the order of addition of said compounds (i), (ii) and (iii) to the receptacle being unimportant.

In other words, in the event that the aqueous gel of step a) takes into consideration the presence of at least one endogenous polyamine, steps a) and b) of the process according to the invention are then carried out concomitantly.

According to a first embodiment variant, this aqueous gel can be formed by introduction of the aqueous medium and of the hyaluronic acid into the receptacle, with simultaneous and/or consecutive homogenization of the mixture thus formed, and then, where appropriate, addition of the crosslinking agent with simultaneous and/or consecutive homogenization.

According to a second embodiment variant, this aqueous gel can be obtained by introduction of the aqueous medium, of the hyaluronic acid and of the crosslinking agent into the receptacle, with simultaneous and/or consecutive homogenization of the mixture thus formed.

This second embodiment variant is advantageous in that a single homogenization step is carried out.

Advantageously, this step of forming the aqueous gel can be carried out at a temperature below 35° C., preferably at a temperature ranging from 15 to 25° C., and better still at an ambient temperature.

The aqueous gel considered in step a) is advantageously homogeneous.

This quality is guaranteed by an operation in which the aqueous gel is homogenized, said operation possibly constituting a step preliminary to step a).

The purpose of this operation, optionally carried out in the presence of the crosslinking agent, is more particularly to hydrate and completely homogenize the hyaluronic acid in the aqueous medium and, where appropriate, the crosslinking agent, and thus to contribute to the optimization of the qualities of the expected crosslinked gel.

Indeed, for obvious reasons, the homogeneity of the crosslinked gel is closely linked to the homogeneous nature of the gel before crosslinking.

The homogenization is considered to be satisfactory when the solution obtained has a homogeneous colouration, without agglomerates, and a uniform viscosity. It can advantageously be carried out under mild operating conditions in order to prevent degradation of the hyaluronic acid chains.

This step is all the more important when the hyaluronic acid has a high molecular weight. The hydration of such a compound then in fact has a tendency to generate the formation of a solution of high viscosity in which the appearance of agglomerates is commonly observed.

As emerges from the aforementioned, the mixture formed in step b), or even, where appropriate, the aqueous gel of step a) when it takes into consideration the presence of the crosslinking agent, is subsequently subjected to a crosslinking reaction, illustrated by step c) of the process for preparing a crosslinked hyaluronic acid gel according to the invention.

As previously indicated, this crosslinking is carried out under conditions favourable to the coupling of said hyaluronic acid and of said endogenous polyamine(s).

The favourable conditions to be retained in order to induce this coupling, and therefore the crosslinking reaction, can depend on the molecular weight of the hyaluronic acid, on the aqueous medium and on the nature of the crosslinking agent, in this case completely or partially formed by an endogenous polyamine.

These favourable conditions can in particular be reflected by the presence of at least one activator, where appropriate combined with at least one auxiliary coupling agent, as indicated above.

As previously indicated, the step of adding the activator and, where appropriate, the auxiliary coupling agent, can preferably be carried out jointly with the crosslinking step c).

However, according to one particular embodiment, the activator and, where appropriate, the auxiliary coupling agent is (are) added before the crosslinking step c), and more particularly before the step of adding at least one endogenous polyamine.

According to another embodiment, this step of adding the activator and, where appropriate, the auxiliary coupling agent is carried out jointly with step b), in which case step b) is then carried out jointly with the crosslinking step c).

Moreover, the degree of crosslinking also depends on the duration of the crosslinking step applied to the mixture obtained at the end of step b). The longer the time, the higher the degree of crosslinking, with, however, an optimum that is not to be exceeded, otherwise there is a risk of degrading the hyaluronic acid.

Thus, when the crosslinking of the hyaluronic acid is carried out in the presence of EDC and of HOBt, the crosslinking step c) can be carried out over a period ranging from 30 minutes to 72 hours, preferentially from 3 to 24 hours.

As previously described, the stopping of the crosslinking (step e) can occur before, jointly with or after the step d) of recovering the gel.

Such a step e) may require exposing the crosslinked gel or the gel undergoing crosslinking, or even the receptacle containing it, to conditions favourable to stopping said crosslinking, or else to conditions capable of stopping the formation of bonds between the various polysaccharide chains.

This step can be initiated naturally if all the reagents are consumed during step c), or promoted by a purification step which brings the gel back to physiological pH and eliminates the unreacted residual reagents.

According to one preferred embodiment variant, step e) is carried out before step d).

According to one particularly preferred embodiment, the process according to the invention uses (i) sodium hyaluronate, (ii) spermine, as crosslinking agent, and (iii) EDC, as activator, in combination with HOBt, as auxiliary coupling agent.

For obvious reasons, the crosslinked gel obtained at the end of the process of the invention is not generally directly injectable because the corresponding aqueous formulation may not be compatible with physiological conditions, nor have a suitable pH.

Thus, one or more additional steps, known to those skilled in the art, may be carried out.

More particularly, a step of purifying the gel according to the invention makes it possible to bring the latter back to physiological pH and to eliminate the unreacted residual reagents.

This purification step may in particular be represented by a dialysis step. What is more, subsequent steps of homogenization, of incorporation of noncrosslinked hyaluronic acid and, optionally, of fractionation may also be carried out in order to further improve the qualities of the implant, according to the knowhow of those skilled in the art. The gel must be formulated physiologically through the presence of salts in amounts equivalent to those of the injected medium.

Finally, the resulting hydrogel may be packed into syringes under controlled atmosphere conditions, it being possible for said syringes to then undergo a sterilization step, preferably heat sterilization.

Composition

According to another aspect, as indicated above, of the present invention, the latter also relates to a sterile injectable dermatological composition comprising, in a physiologically acceptable medium, at least one crosslinked hyaluronic acid gel as defined above.

By virtue of its injectable nature, a composition according to the invention therefore necessarily comprises a physiologically acceptable medium.

The term "physiologically acceptable medium" is intended to mean a medium which is devoid of toxicity and is compatible with the injection and/or the application of the composition in or through keratin materials.

The composition may comprise a physiologically acceptable solvent or a mixture of physiologically acceptable solvents.

The composition may comprise a physiologically acceptable aqueous medium.

By way of aqueous medium that is suitable for the invention, mention may, for example, be made of water.

By way of isotonic agents that are suitable for the preparation of a composition that is suitable for the invention, mention may be made of sugars and sodium chloride.

According to yet another aspect, as indicated above, of the present invention, the latter relates to a dermatological or cosmetic composition comprising at least one crosslinked hyaluronic acid gel according to the invention.

This embodiment, which is not limited in terms of route of administration, consequently permits the administration of said composition topically.

Additional Active Agents

A composition according to the invention may also comprise at least one additional active agent that is compatible with use in the field of sterile injectable compositions.

Among the additional active agents usable in the present invention, mention may be made of antioxidants, amino acids, vitamins, minerals, nucleic acids, coenzymes, adrenaline-containing derivatives, and mixtures thereof.

By way of antioxidants, mention may in particular be made of glutathione, ellagic acid, spermine, resveratrol, retinol, L-carnitine, polyols, polyphenols, flavonols, theaflavins, catechins, caffeine, ubiquinol, ubiquinone, and a mixture thereof.

By way of amino acids, mention may in particular be made of arginine, isoleucine, leucine, lysine, glycine, valine, threonine, proline, methionine, histidine, phenylalanine, tryptophan, and a mixture thereof.

By way of vitamins or derivatives thereof, mention may in particular be made of vitamins E, A, C and B, more particularly vitamins $B_6$, $B_8$, $B_4$, $B_5$, $B_9$, $B_7$ and $B_{12}$, and better still pyridoxine.

By way of minerals, mention may in particular be made of the zinc salts, magnesium salts, calcium salts, potassium salts, manganese salts, sodium salts, and a mixture thereof.

By way of nucleic acids, mention may in particular be made of derivatives of adenosine, of cytidine, of guanosine, of thymidine, of cytodine, and a mixture thereof.

By way of coenzymes, mention may in particular be made of coenzyme Q10, CoA, NAD, NADP, and a mixture thereof.

By way of adrenaline-containing derivatives, mention may particularly be made of adrenaline and noradrenaline.

Moreover, a composition according to the invention may also comprise any excipient normally used in the technical field considered, such as, for example, sodium dihydrogen phosphate monohydrate and/or dihydrate, and sodium chloride, in physiologically suitable contents.

The amounts of additional active agents and/or excipients depend of course on the nature of the compound considered, on the desired effect, and on the destination of the composition according to the invention.

These parameters are among the general skills of those skilled in the art.

Advantageously, a composition according to the invention may comprise from 2 ppm to 10 000 ppm, preferably from 5 to 1000 ppm, and better still from 50 to 500 ppm of additional active agents and/or excipients relative to the total weight of said composition.

Moreover, it is known that the injection of a composition dedicated to filling wrinkles often causes a painful sensation for the patient.

Thus, according to one particular embodiment, a composition according to the invention may also comprise at least one anaesthetic agent.

An anaesthetic agent has precisely the advantage of reducing, or even eliminating, the painful sensation felt by the patient at the time of and/or following the administration of a composition in accordance with the invention.

What is more, the inventors have noted that the presence of such a compound does not raise any risk of incompatibility with the other compounds used in a composition according to the invention, and in particular with the hyaluronic acid.

An anaesthetic usable in the present invention may be chosen from ambucaine, amolanone, amylocaine, articaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodone, dycyclonine, ecgonidine, ecgonine, ethyl chloride, etidocaine, beta-eucaine, euprocine, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or a salt thereof.

More particularly, an anaesthetic usable in the present invention may be chosen from articaine, benzocaine, bupivacaine, chloroprocaine, lidocaine, mepivacaine, prilocaine, procaine, ropivacaine, and tetracaine.

Preferably, the anaesthetic may be lidocaine, and better still lidocaine hydrochloride.

A composition according to the invention may advantageously comprise from 0.01% to 1% by weight, preferably from 0.1% to 0.5% by weight of anaesthetic(s), relative to the total weight of said composition.

According to one particular embodiment, a gel or a composition according to the invention, in addition to the hyaluronic acid in a crosslinked form, may also comprise hyaluronic acid in a noncrosslinked form.

Such a combination of hyaluronic acid in free and crosslinked form immediately results in moisturization and maintenance of the volume of the skin. Furthermore, it induces a boosting of dermal fibroblasts, mainly due to the presence of free hyaluronic acid, and this boosting of fibroblasts is prolonged over time as the crosslinked hyaluronic acid is degraded in vivo. From a functional point of view, the presence of noncrosslinked hyaluronic acid makes it possible to significantly improve the forces of extrusion of the gel through a needle, thus facilitating the force to be applied by the practitioner for injecting the product.

Administration of the Sterile, Injectable Crosslinked Hyaluronic Acid Gel or Dermatological Composition A crosslinked hyaluronic acid gel or a composition according to the invention can be injected using any one of the modes known to those skilled in the art.

In particular, a gel or a composition according to the invention may be administered by means of an injection device suitable for an intraepidermal and/or intradermal and/or subcutaneous injection.

The injection device may be chosen from a syringe, a set of microsyringes, a hydraulic, laser device, an injection gun, a needleless injection device, or a microneedle roller.

Preferably, the injection device may be chosen from a syringe or a set of microsyringes.

Preferably, such a means may be a hypodermic needle or a cannula.

A needle or cannula according to the invention may have a diameter ranging from 18 to 34 G, preferably between 25 and 32 G, and a length ranging from 4 to 70 mm, and preferably from 4 to 25 mm.

The needle or cannula is advantageously disposable.

Advantageously, the needle or cannula is combined with a syringe or any other device for delivering said injectable composition through the needle or the cannula. According to one embodiment variant, a catheter may be inserted between the needle/the cannula and the syringe.

In a known manner, the syringe may be operated manually by the practitioner or else by means of a syringe support, such as guns.

Kit

According to another aspect of the present invention, the latter relates to a kit comprising:
- a packaging containing at least one dose of a crosslinked hyaluronic acid gel or of a composition according to the invention; and
- a device for injecting in or through the skin or a device for microperforation of the skin, dedicated to the administration of said dose.

The packaging is suitable for the storage of at least one dose of the gel or of the composition according to the invention.

The packaging may be arranged so to allow, moreover, said gel or said composition to be sampled.

Thus, according to a first embodiment, said packaging is scored so as to allow said gel or said composition to be sampled.

For example, it may be in the form of an ampoule, a bottle or a capsule, in particular a soft capsule.

Preferably, the packaging may be single-dose and/or have a scored end.

According to a second embodiment, said packaging has a cap which allows hermetic sealing during storage and which can be pierced by a needle or cannula at the time of use.

With regard to the injection device, it may be as previously defined and preferably be disposable.

Preferably, the injection device is suitable for an intraepidermal and/or intradermal and/or subcutaneous injection.

Preferentially, said device is suitable for the mesotherapy technique.

Use

According to yet another aspect of the present invention, the latter relates to the use of a crosslinked hyaluronic acid gel or of a composition according to the invention, for preventing and/or treating the cutaneous signs of chronological ageing and/or the cutaneous signs which are induced by external factors such as stress, tobacco and/or prolonged exposure to UV radiation.

A crosslinked hyaluronic acid gel or a composition according to the invention is also advantageous in that it can be used for preventing and/or treating a modification of the surface appearance of the skin, a modification of the viscoelastic or biomechanical properties of the skin, a decrease in cell energy metabolism, or dehydration of the skin.

A crosslinked hyaluronic acid gel or a composition according to the invention is again advantageous in that it can be used for filling skin volume defects, in particular wrinkles, and/or restoring the radiance of the skin.

Treatment Process

According to another aspect of the present invention, the latter relates to a cosmetic skin treatment process comprising at least one step of administering, in or through the skin, a crosslinked hyaluronic acid gel or a composition according to the invention.

According to one particular embodiment, the administration step can be repeated on all or part of the surface to be treated. The repetition of the injections makes it possible to create a layering such that the composition according to the invention is distributed homogeneously in the skin region to be treated.

According to one particular embodiment, the skin regions advantageously treated by means of a process of the invention may be the skin and the lips, and in particular the skin of the face, of the neck, of the neckline, of the hands, of the scalp, of the abdomen and/or of the legs.

A gel or a composition according to the invention may advantageously be injected at the level of the wrinkles and fine lines.

There are several injection techniques.

By way of usable techniques, mention may be made of the "multiple bolus" technique which consists in performing injections in the superficial dermis of on average 0.05 ml of a composition according to the invention, called a bolus, said boluses each being about 1 cm apart. This technique is in particular recommended for the face and the neckline.

Mention may also be made of the "backtracking" technique which consists in performing linear tracking injections in the superficial dermis, in introducing the needle with a 45° angle along the skin depression and then depositing the composition according to the invention in the superficial dermis while gently withdrawing the needle.

Finally, mention may be made of the "multipuncture" technique which consists in performing a burst of multiple injections of small amounts of composition according to the invention in the epidermis. The injection points are very close together, for example approximately every 3 mm, and are distributed uniformly over the surface to be treated or by forming a line along the wrinkle. This technique is in particular recommended for unifying the complexion.

The treatment process in accordance with the invention also proves to be advantageous for preventing and/or treating the cutaneous signs of ageing or of photoageing, in particular chosen from wrinkled skin, skin exhibiting a modification of its viscoelastic or biochemical properties, skin exhibiting a modification in the cohesion of its tissues, thinned skin, skin exhibiting a modification of its surface appearance, slackening of the skin.

The treatment process in accordance with the present invention also proves to be advantageous for preventing and/or treating a decrease in cell energy metabolism or dehydration of the skin.

The treatment process in accordance with the present invention also proves to be advantageous for filling skin volume defects, in particular wrinkles, and/or restoring the radiance of the skin.

The treatment process in accordance with the present invention can preferably be carried out in an epidermal, dermo-epidermal and/or dermal, or even subcutaneous, region.

Throughout the present application, the expression "comprising a" is synonymous with "comprising at least one" and "between . . . and . . . " and "ranging from . . . to . . . " should be understood to mean limits inclusive.

The following examples are given by way of nonlimiting illustration of the present invention.

EXAMPLES

Example 1: Protocol for Preparing a Hyaluronic Acid Gel Crosslinked with Spermine as Crosslinking Agent Hyaluronic acid is dissolved at a concentration of 3% (by weight) in water. After obtaining a homogeneous solution, a solution containing spermine (the one ≥96% sold by the company Sigma-Aldrich under the name Sigma), EDC as activator (N-(3-dimethylaminopropyl)-N'-ethylcarbodiimide hydrochloride ≥98.0% sold by the company Sigma-Aldrich under the name Fluka) and HOBt as auxiliary coupling agent (1-hydroxybenzotriazole hydrate, ≥97% sold by the company Sigma-Aldrich under the name Aldrich) is added to the hyaluronic acid solution. The volume of this solution is defined so as to obtain an overall mixture containing 2.3% of hyaluronic acid.

The pH of this solution is adjusted so as to obtain a pH of the overall mixture of between 5.5 and 6.5 before reaction, by using a dilute solution of HCl or of NaOH.

The amounts of reagents are adjusted according to the desired degree of modification.

They range between $5 \times 10^{-3}$ and $2 \times 10^{-2}$ mol/mol of hyaluronic acid repeat units for the polyamine, and between 0.5 and 1 mol/mol of hyaluronic acid repeat units for the activator and the auxiliary coupling agent involved in the coupling reaction. The stoichiometries used are indicated in the examples given.

For the crosslinking, the aqueous gel is exposed for 7 to 24 h at 25° C.

After crosslinking, the gel obtained is purified by means of several dialysis baths over a period of from 2 to 3 days and, if necessary, adjusted to physiological pH.

The aqueous gel obtained after washing comprises a hyaluronic acid concentration close to 20 mg/g.

In order to facilitate the extrusion forces for passing the gel through a needle, noncrosslinked hyaluronic acid is then incorporated into and homogenized in the gel obtained above.

The sterilization is carried out in an autoclave (wet heat) at T°≥121° C., so as to obtain an F0>15 (sterilizing value).

Example 2: Preparation of Crosslinked Hyaluronic Acid Gels which are in Accordance with the Invention (with Spermine) and Comparative (with HMDA)

Three crosslinked hyaluronic acid gels are prepared on the basis of the protocol defined in Example 1 above.

For these three gels, n HOBt=n EDC=n HA.

These three gels differ from one another by virtue of the nature of the polyamine under consideration and/or the "polyamine/hyaluronic acid" ratio, as illustrated in Table 1 hereinafter. The final column [HA] indicates the hyaluronic acid concentration of the gels obtained.

TABLE 1

| Gel crosslinked | Crosslinking agent | Stoichiometry: n polyamine/n HA | [HA], mg/g |
|---|---|---|---|
| A (comparative) | HMDA* | 0.100 | 21 |
| B | Spermine | 0.020 | 21 |
| C | Spermine | 0.010 | 21 |

*HMDA = hexamethylenediamine
n HOBt = n EDC = n HA

1) Characterization of the Degree of Modification of the Gels A, B and C

Sample Preparation Protocol

The gels A, B and C are washed/precipitated with isopropanol.

The solids obtained are dried and then solubilized in $D_2O$, and treated in the presence of hyaluronidase (type VI-S, Sigma, 3 kU) in 1 ml of $D_2O$ for degradation of the gel, in order to obtain a liquid matrix for analysis.

The homogeneous mixture obtained is then analysed by $^1$H NMR.

Measurement of the Degree of Modification

The characterization of the respective degrees of modification to the gels A, B and C is carried out by NMR spectroscopy.

For the polyamines, the $^1$H proton peaks for HMDA at 1.34 ppm and for spermine at 1.73 ppm are retained as references.

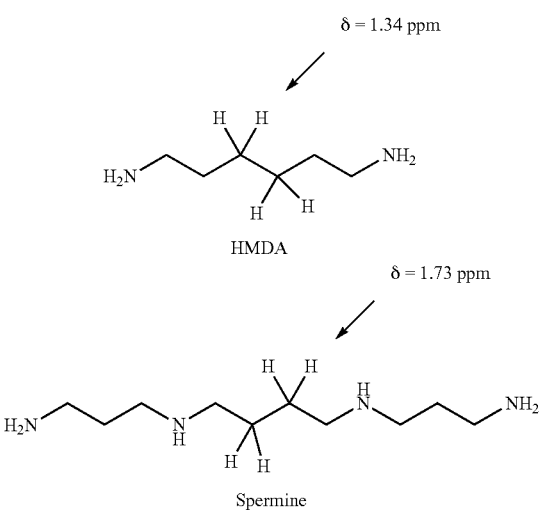

HMDA

Spermine

The degree of modification of each of the three crosslinked hyaluronic acid gels is then characterized using the integral of these reference peaks according to the following formula:

$$\text{Degree of modification} = \frac{\left(\frac{\text{Integral } \delta_{H\text{-reference}}}{X}\right)}{\left(\frac{\text{Integral } \delta_{Acetamide}}{3}\right)}$$

X: number of protons of the peak retained for the measurement, i.e. 4 for spermine and HMDA.

δ-Acetamide: shift corresponding to the acetamide peak of HA, therefore comprising 3 protons.

The NMR analysis is carried out on a Bruker Avance 1 spectrometer operating at 400 MHz ($^1$H).

The various results and observations are summarized in the following Table 2:

TABLE 2

| GEL | δH-ref (ppm) | X | Degree of modification (%) |
|---|---|---|---|
| A (HMDA control) | 1.34 | 4 | 5.0 |
| B | 1.73 | 4 | 0.7 |
| C | 1.73 | 4 | 1.0 |

It emerges from Table 2 above that the degrees of modification of the crosslinked gels B and C in accordance with the invention are, compared with those of the control gel A, significantly reduced.

The hyaluronic acid crosslinked with spermine is therefore less modified than the one resulting from the crosslinking with HMDA.

2) Characterization of the Mechanical Properties a) The viscoelastic properties of the gels A, B and C are characterized via the measurement of their elastic modulus G' (in Pa) and of their phase angle δ (°), measured at 1 Hz for a stress of 5 Pa.

Table 3 hereinafter represents the values measured.

TABLE 3

| | Amplitude sweep (cone/plate) | | |
|---|---|---|---|
| Gel | G' (Pa) measured at τ = 5 Pa | δ (°) measured at τ = 5 Pa | τ (Pa) measured at cross-over |
| A (HMDA control) | 64 | 48.2 | 90 |
| B | 318 | 10.8 | 510 |
| C | 227 | 18.1 | 590 |

The control gel A, although crosslinked with a polyamine (HMDA), is not sufficient since, although the degree of modification of the hyaluronic acid is high, its mechanical properties are weak.

Despite a reduced degree of modification, the gels B and C exhibit, on the other hand, a rheological behaviour which is significantly improved compared with the comparative gel A.

b) The resistance to sterilization of the gels A, B and C is determined via the characterization of the loss of elastic modulus G' (in Pa) of these gels after exposure to a sterilization carried out in an autoclave (wet heat) at T°≥121° C., so as to obtain an F0≥15 (sterilizing value).

Table 4 hereinafter represents the values measured.

TABLE 4

| Gel | Amplitude sweep (cone/plate) measured at t = 5 Pa Loss G' (%) |
|---|---|
| A (HMDA control) | 60% |
| B | 23% |
| C | 24% |

The control gel A is once again not satisfactory since it exhibits poor resistance to sterilization compared with the gels B and C.

The invention claimed is:

1. A process for preparing a crosslinked gel of hyaluronic acid or a salt thereof, comprising the steps:
    a) providing an aqueous gel of hyaluronic acid or of a salt thereof, in the noncrosslinked state,
    b) bringing the gel obtained in step a) into contact with an effective amount of at least one endogenous polyamine to form a mixture, wherein said at least one endogenous polyamine is used in a content between 0.1% and 3% by number of moles of the at least one endogenous polyamine relative to the number of moles of hyaluronic acid,
    c) crosslinking said mixture formed in step b), said crosslinking being carried out under conditions favourable to the covalent coupling of said hyaluronic acid and of said at least one endogenous polyamine to form a crosslinked hydrogel, and
    d) recovering said crosslinked hydrogel, wherein said crosslinked hydrogel has a degree of modification of less than or equal to 1%, the degree of modification being the ratio between the number of moles of endogenous polyamine attached to the hyaluronic acid and the number of moles of hyaluronic acid forming said crosslinked hydrogel.

2. The process according to claim 1, wherein said process also comprises a step e) of stopping the crosslinking, consisting of exposing the crosslinked hydrogel to conditions capable of stopping the crosslinking thereof, wherein the stopping step is carried out before, jointly with or after the recovering step d).

3. The process according to claim 1, wherein the at least one endogenous polyamine is selected from the group consisting of spermidine, spermine, and a mixture thereof.

4. The process according to claim 1, wherein the hyaluronic acid or a salt thereof is used in a content of between 0.5% and 12% by weight relative to the total weight of the mixture obtained at the end of step b).

5. The process according to claim 1, wherein the crosslinking is carried out in the presence of a supplementary crosslinking agent.

6. The process according to claim 1, wherein the coupling is carried out in the presence of at least one activator and, optionally combined with at least one other agent as auxiliary coupling agent.

7. The process according to claim 1, wherein the process uses (i) sodium hyaluronate, (ii) spermine, as crosslinking agent, and (iii) 1-ethyl-3-(3-dimethylaminopropyl)carbodiimide (EDC) in combination with N-hydroxybenzotriazole (HOBt), as, respectively, activator and auxiliary coupling agent.

* * * * *